United States Patent [19]

Amrani

[11] 4,210,580

[45] Jul. 1, 1980

[54] PROCESS FOR SEPARATION AND ISOLATION OF AHF AND FIBRONECTIN FROM BLOOD PLASMA

[76] Inventor: David Amrani, 75 Rumson Rd., Staten Island, N.Y. 10304

[21] Appl. No.: 49,965

[22] Filed: Jun. 19, 1979

[51] Int. Cl.$^2$ .................. A23J 1/06; A61K 35/16; C07G 7/00
[52] U.S. Cl. ........................ 260/112 B; 424/101
[58] Field of Search .................. 260/112 B; 424/101

[56] References Cited

U.S. PATENT DOCUMENTS

| | | | |
|---|---|---|---|
| 3,803,115 | 4/1974 | Fekete et al. | 260/112 B |
| 3,842,061 | 10/1974 | Andersson et al. | 260/112 B |
| 3,920,625 | 11/1975 | Andersson et al. | 260/112 B |
| 3,973,002 | 8/1976 | Hagan et al. | 260/112 B |
| 4,022,758 | 5/1977 | Andersson et al. | 260/112 B |
| 4,069,216 | 1/1978 | Shanbrom | 260/112 B |
| 4,081,431 | 3/1978 | Stephan et al. | 260/112 B |
| 4,086,218 | 4/1978 | Shanbrom et al. | 260/112 B |
| 4,093,608 | 6/1978 | Iga et al. | 424/101 X |
| 4,104,266 | 8/1978 | Wickerhauser | 260/112 B |

OTHER PUBLICATIONS

Proc. 7th Congress European Soc. Haematology, London, 1959, Part II, pp. 587–593, (1960), Blombäck et al.
J. Biol. Chem. (1973), 248 (24), pp. 8429–8433, Sawyer et al.

*Primary Examiner*—Howard E. Schain
*Attorney, Agent, or Firm*—Spellman, Joel & Pelton

[57] ABSTRACT

A process for the separation and isolation of AHF and fibronectin from blood plasma by adding a sulfated mucopolysaccharide to blood plasma to a concentration of 0.15–0.25 mg/ml of plasma, cooling the plasma to 0° C.–15° C. centrifuging the plasma to isolate a precipitate which forms and then removing the AHF-rich supernatant liquid from the precipitate.

The precipitate is washed in a slightly basic solution of dilute salts and then dissolved in a buffered solution of chaotrophic salts of the Hofmeister series having an ionic strength from 0.01–1. Fibronectin is then separated, by chromotographic means, from the dissolved precipitate, which contains fibronectin and fibrinogen.

In a preferred embodiment, 0.20 mg of sodium heparin per milliliter of human plasma is employed with the heparinized plasma solution cooled for 3 hours at a temperature of 2° C.–4° C.

7 Claims, No Drawings

PROCESS FOR SEPARATION AND ISOLATION OF AHF AND FIBRONECTIN FROM BLOOD PLASMA

BACKGROUND OF THE INVENTION

This invention is concerned with a method for obtaining significant amounts of certain components of blood plasma.

The important components of blood plasma with which the process of this invention is primarily concerned are the antihemophilia factor (AHF) and plasma fibronectin [cold-insoluble globulin - CIg]. Each of the components obtained according to the process of this invention is extremely valuable in therapeutic applications. The AHF is known, of course, as the single significantly effective agent for use in treating hemophilia A.

It has been demonstrated in recent years that the fibronectin (CIg) component of human plasma is especially useful in speeding tissue recovery in trauma, particularly burns. The affinity of fibronectin to collagen and/or fibrin may be of significance in the mode of its action.

The infusion of plasma fractions enriched with fibronectin has been effective in reducing general septsis from severe trauma and burns. It has been found that a reduction in the body's level of fibronectin occurs following trauma, and that the sooner fibronectin is restored to normal levels, the faster recovery takes place; presumably related to an increase in the removal of damaged tissues, reduction of infection, and general wound healing.

Of concern to the growing application of fibronectin therapy is the depletion of plasma available for the isolation of AHF. This has vastly increased the need for an effective and efficient large scale process for separating plasma fractions of predominating fibronectin from the fractions of predominantly AHF activity.

Past methods have suffered from difficulties in effectively separating the desired constituents and isolating them on a large scale.

The present invention utilizes a number of individually known steps in combination with new approaches to develop a new overall process for the large scale isolation and purification of fibronectin (CIg) and AHF from blood plasma.

In the past, the separation of these components has been carried out on only small scale levels of a milliliter of plasma up to one or two hundred milliliters of plasma. No satisfactory method has previously been available for the processing of significant amounts of plasma such as over 0.5 liters and even up to 1–5 liters.

It is well know that many unpredicted difficulties are usually encountered in attempts to scale up laboratory experimental procedures with plasma to even minimal commercial levels.

In the past, the attempted recovery of the fibronectin from the cryoprecipitate utilized phosphate and/or Tris (hydroxmethyl) aminomethane type of buffer salts and resulted in low percentage recoveries of fibronectin.

SUMMARY OF THE INVENTION

According to the present invention, there is provided a process for the separation of the fibronectin-rich (CIg) fraction and the AHF-rich fraction of blood plasma by cryoprecipitation in the presence of a very specific concentration of certain sulfated mucopolysaccharides such as heparin, alginic acid sulfate, chitin sulfate, polymannuronic acid sulfate and chondroitin sulfate and the subsequent purification of the fibronectin fraction by chromatographic separations utilizing a unique buffer system.

According to the process of the present invention, very significantly greater percentages of both the fibronectin and AHF components are recovered compared to existing methods. In addition, the process of the present invention, while applicable for small scale plasma separations to which prior methods have generally been limited, is unexpectedly useful in separating the AHF and fibronectin fractions on a large scale, i.e., more than 0.5 liters of blood plasma, with sums of 1–2 liters being accomplished with ease. Most significantly, the extremely high percentage recovery of AHF and fibronectin is applicable even when using the process with the larger volumes of blood plasma.

Heparin is the preferred polysaccharide to use and the recommended concentration is from 0.15 to 0.25 mg/ml of plasma with the preferred concentration being about 0.20 mg/ml.

The heparin is added to the plasma, which is then cooled to 0° C.–15° C. and preferably 2°–4° C. for at least one hour, preferably for at least three hours.

A fine granular precipitate forms and is collected by centrifugation. A speed of 3,000–10,000 xg for 15–20 minutes is generally convenient and efficient.

Approximately, 80–90% of the fibronectin component of the plasma is precipitated in this manner.

The supernatant liquid, which is rich in AHF, may be freeze-dried or frozen to prevent loss of activity prior to use or further processing.

The precipitate of the fibronectin fraction is washed gently with an ice-cold wash of several dilute salts such as $NaH_2PO_4$ and NaCl at a slightly basic pH and recentrifuged for ten minutes at 2°–4° C., preferably three times.

After washing, there is gently added to the precipitate a buffer solution of a chaotrophic salt of the Hofmeister series having an ionic strength between 0.01–1, preferably 0.05–0.5 with 0.2 ionic strength as representative of the most used level. Chaotrophic salts such as KSCN and KI buffered in the pH range of 6–8 are preferred, with a solution of 0.2 M KSCN, 0.1 M Tris-Cl at pH 7.5 as most often used to dissolve the precipitate. The buffer is generally warmed to about 37° C.

The precipitate mixture is then warmed for 1–2 hours at about 37° C. It is important not to disturb the precipitate at this point to avoid irreversible aggregation of the fibronectin-fibrinogen-heparin complex.

After the warming period, the precipitate is partially dissolved. Then additional buffer solution is added to dilute to a final concentration of 0.05 M KSCN, bringing the protein concentration to 2–4 mg/ml.

The dissolved fibronectin and fibrinogen protein complex is then separated chromatographically. The solution is applied to a DEAE cellulose (Whatman DE-23) column.

The fibrinogen is usually eluted with 0.05 M KSCN, 0.1 M Tris-Cl at a pH of about 6–8, preferably about 7.5. When absorbance returns to a baseline level, a linear gradient of 0.05 M KSCN, 0.1 M Tris-Cl at pH 7.5 (75–300 ml/chamber) is applied, and finally a wash of 0.5 M KSCN, 0.1 M Tris-Cl at a pH of about 7.5. Heparin separates from the fibronectin at the end of the gradient.

Also, the fibronectin can be eluted with a single buffer after the fibrinogen has been removed. Any buffer of at least 0.25 ionic strength and a pH range of 6-8 may be employed, such as 0.25 M NaH$_2$PO$_4$-Tris pH 7.0 or 0.3 M KSCN, 0.1 M Tris-Cl pH 7.5 and preferably 0.25 M Phosphate-Tris pH 7.0 or 0.3 M KSCN, 0.1 M Tris-Cl pH 7.5 to remove the fibronectin from the resin with a minimal amount of contaminating heparin. However, there is a 10-20% decrease in recovery of fibronectin at this phase. Approximately 45-50% recovery of fibronectin is usually obtained with either system.

As to the heparin supernatant fraction, each liter is mixed with an anion exchange resin, for example, 20-30 grams of DEAE cellulose with micro-crystalline binder (such as Heparasorb, General Diagnostics) for 10-15 minutes. The resin is then removed by constant flow centrifugation or macrofiltration.

The supernatant liquid recovered usually has 90-95% of the original procoagulant activity. The removal of heparin is confirmed by a thrombin time determination.

In this specification and the claims, it should be understood that the term blood plasma includes blood plasma itself and cryoprecipitate which has been dissolved in dilute salt buffers.

The following representative embodiments will further illustrate the nature of the invention.

ILLUSTRATIVE EMBODIMENTS

EXAMPLE 1

1.5 Liters of human blood plasma are warmed at 37° C. for 30 minutes. 1.6 mls Of a 200 mg/ml sodium heparin solution (sigma 167 $\mu$/mg) is mixed with the plasma and the plasma then cooled at 4° C. for 18 hours (overnight) and a precipitate formed. The precipitate is collected by centrifugation at 4° C. for 30 min. at 9,500 xg. The supernatant liquid is saved.

The precipitate is washed with 1 liter of 0.05 M NaH$_2$PO$_4$, 0.1 M NaCl pH 7.2 at 4° C.; centrifuged for 30 minutes at 9,500 xg and the wash discarded. The precipitate is dissolved in 120 mls of 0.2 M KSCN, 0.1 M Tris-Cl at pH 7.5. The total protein content is 484 with 4.03 mg/ml concentration. The dissolved precipitate is diluted with 0.1 M Tris-Cl pH 7.5 to a final concentration of 0.05 M KSCN.

The diluted sample is applied to a 2.5×40 cm DEAE cellulose column pre-equilibrated with 0.05 M KSCN, 0.1 M Tris-Cl pH 7.5 and the column washed with 0.05 M KSCN buffer until the absorbance returned to baseline. A stepwise buffer, 0.25 M Tris-PO$_4$, pH 7.0 is used rather than a gradient to elute the fibronectin. A total of 176.5 mg of fibronectin is eluted which represents about 40-45% recovery of total fibronectin, assuming a 250-300 mg/liter starting concentration.

EXAMPLE 2

300 mls Of human blood plasma are warmed to 37° C. To the warm plasma, NaN$_3$ os added to a dilution of 0.02%, and Trasylol to a dilution of 2 mg/ml. To this solution is added sodium heparin to obtain a final concentration of 0.2 mg/ml of heparin. The solution is stirred until the materials are completely dissolved. The solution is cooled in a water bath at 2° C. for three hours and then centrifuged at 10,000 xg for 30 minutes at 2° C. The supernatant liquid contains 90-95% of the AHF material.

The precipitate is washed with a cold solution of 0.05 M NaH$_2$PO$_4$, 0.1 M NaCl, at a pH 7.2. The solution is recentrifuged and washed twice again. The precipitate is then dissolved in 0.05 M KI, 0.1 M Tris at a pH of 7.5 with 0.02% NaN$_3$, and 2$\mu$/ml Trasylol to a concentration of 5 mg/ml.

The dissolved precipitate is applied to a 1.5×30 cm DEAE cellulose column and the fibrinogen is eluted with a 0.05 M KI, 0.1 M Tris-Cl pH 7.5 buffer. The fibronectin (CIg) is then eluted with a linear gradient of 0.05 M KI, 0.1 M Tris-Cl pH 7.5 buffer. The fibronectin peak was pooled into three fractions adding up to 83 mg from a starting amount of 128 mg, yielding a 65% recovery.

EXAMPLE 3

The procedure of Example 1 is repeated using 0.15 mg/ml of heparin with satisfactory results although the percentage of fibronectin isolated is somewhat less.

EXAMPLE 4

The procedure of Example 1 is repeated but using 0.25 mg/ml of sodium heparin.

While the invention has been explained by a detailed description of certain specific embodiments, it is understood that various modifications and substitutions can be made in any of them within the scope of the appended claims which are intended also to include equivalents of such embodiments.

What is claimed is:

1. A process for the separation and isolation of AHF and fibronectin fractions from blood plasma comprising:
   (a) adding a sulfated mucopolysaccharide to blood plasma to a concentration of 0.15-0.25 mg/ml of plasma;
   (b) then cooling said plasma to 0° C.-15° C.;
   (c) centrifuging the plasma to isolate a precipitate which forms;
   (d) removing the supernatant liquid from the precipitate, said supernatant liquid being rich in AHF;
   (e) washing the precipitate in a slightly basic solution of dilute salts;
   (f) thereafter dissolving said precipitate in a buffered solution of chaotrophic salts of the Hofmeister series having an ionic strength from 0.01-1;
   (g) and thereafter separating said fibronectin from the dissolved precipitate which contains fibronectin and fibrinogen by chromotographic means.

2. A process as claimed in claim 1, wherein said mucopolysaccharide is heparin.

3. A process as claimed in claim 2, wherein said heparin is present in an amount of 0.20 mg/ml of plasma.

4. A process as claimed in any of the preceding claims, wherein said blood plasma is cooled to 2° C.-4° C. for 30 minutes to 3 hours.

5. A process as claimed in any of the preceding claims, wherein said chaotrophic salt has an ionic strength of from 0.05-0.5.

6. A process as claimed in any of the preceding claims, wherein the supernatant liquid is mixed with an anion exchange resin for 10-15 minutes, and thereafter said resin is removed.

7. A process for the separation and isolation of AHF and fibronectin from blood plasma which comprises adding sodium heparin to human blood plasma to obtain a concentration of about 0.20 mg of heparin per milliliter of plasma, then cooling the plasma solution to 2° C.-4° C. for 1-3 hours, thereafter centrifuging the precipitate which forms, removing the supernatant liquid which is rich in AHF, removing the heparin from said AHF-rich fraction, washing said precipitate with a dilute salt solution at a slightly basic pH, thereafter dissolving said precipitate in a buffered solution of chaotrophic salts of the Hofmeister series having an ionic strength of about 0.05–0.5, and finally separating said fibronectin from the fibronectin-fibrinogen mixture by chromotographic means.

* * * * *